(12) United States Patent
Spindler

(10) Patent No.: US 11,234,806 B2
(45) Date of Patent: Feb. 1, 2022

(54) DATA STORAGE ON IMPLANTABLE MAGNETIZABLE FABRIC

(71) Applicant: Cook Medical Technologies LLC, Bloomington, IN (US)

(72) Inventor: Ralf Spindler, Solsberry, IN (US)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 176 days.

(21) Appl. No.: 16/541,758

(22) Filed: Aug. 15, 2019

(65) Prior Publication Data

US 2020/0054437 A1  Feb. 20, 2020

Related U.S. Application Data

(60) Provisional application No. 62/719,354, filed on Aug. 17, 2018.

(51) Int. Cl.
| | | |
|---|---|---|
| *A61F 2/07* | (2013.01) | |
| *A61B 5/00* | (2006.01) | |
| *H03M 5/14* | (2006.01) | |
| *G06K 7/08* | (2006.01) | |
| *G06F 7/40* | (2006.01) | |

(52) U.S. Cl.
CPC ............ *A61F 2/07* (2013.01); *A61B 5/4851* (2013.01); *G06F 7/405* (2013.01); *G06K 7/084* (2013.01); *H03M 5/145* (2013.01)

(58) Field of Classification Search
CPC ................................ G06F 19/00; D03D 15/00
See application file for complete search history.

(56) References Cited

U.S. PATENT DOCUMENTS

| | | | |
|---|---|---|---|
| 6,080,690 A * | 6/2000 | Lebby | .................. D03D 15/258 442/209 |
| 6,334,868 B1 | 1/2002 | Ham | |
| 6,800,089 B1 | 1/2004 | Wang | |
| 6,911,040 B2 | 6/2005 | Johnson et al. | |
| 7,118,592 B1 | 10/2006 | Dang et al. | |
| (Continued) | | | |

FOREIGN PATENT DOCUMENTS

| | | |
|---|---|---|
| CA | 2114891 C | 1/1999 |
| CA | 2340439 C | 2/2000 |
| (Continued) | | |

OTHER PUBLICATIONS

Justin Chan and Shyamnath Gollakota, Data Storage and Interaction using Magnetized Fabric, UIST 2017.

(Continued)

*Primary Examiner* — Yashita Sharma
(74) *Attorney, Agent, or Firm* — Crowell & Moring LLP

(57) ABSTRACT

The disclosure is directed to a system, device and method for data storage on implantable magnetizable fabric. The system includes implantable magnetizable fabric coupled to a graft segment of a prosthesis for being delivered into a body of a subject. The system includes information written on the implantable magnetizable fabric. The system further includes a magnetic detection device capable of, after the prosthesis is delivered into the body of the subject, detecting the implantable magnetizable fabric and accessing at least a portion of the information.

12 Claims, 7 Drawing Sheets

(56) References Cited

U.S. PATENT DOCUMENTS

| | | |
|---|---|---|
| 7,413,573 B2 | 8/2008 | Hartley |
| 7,704,282 B2 | 4/2010 | Disilvestro et al. |
| 7,769,603 B2 | 8/2010 | Jung et al. |
| 7,945,409 B2 | 5/2011 | Furst et al. |
| 8,461,478 B2 | 6/2013 | Chen et al. |
| 8,636,794 B2 | 1/2014 | Casanova et al. |
| 8,721,704 B2 | 5/2014 | Cully et al. |
| 9,861,445 B2 | 1/2018 | Saotome et al. |
| 2002/0096252 A1 | 7/2002 | Lukie |
| 2005/0131519 A1 | 6/2005 | Hartley |
| 2007/0018004 A1* | 1/2007 | Gurovich ............... G06K 7/084 235/493 |
| 2007/0055359 A1 | 3/2007 | Messer et al. |
| 2008/0195193 A1 | 8/2008 | Purdy |
| 2011/0270373 A1 | 11/2011 | Sampognaro et al. |
| 2015/0223899 A1 | 8/2015 | Kieser |
| 2016/0296324 A1 | 10/2016 | Bapat et al. |
| 2017/0112611 A1 | 4/2017 | Edwin et al. |

FOREIGN PATENT DOCUMENTS

| | | |
|---|---|---|
| EP | 0877581 A1 | 5/1997 |
| JP | 2000314045 A | 11/2000 |
| WO | WO2002022024 A2 | 9/2000 |

OTHER PUBLICATIONS

Ernest Rehmatulla Post, Maggie Orth, PR Russo, and Neil Gershenfeld. 2000. E-broidery: Design and fabrication of textile-based computing. IBM Syst. J. 39, 3-4 (Jul. 2000), 840-860.

* cited by examiner writing information on the implantable magnetizable fabric, the information comprising first information comprising information corresponding to at least one of the implantable magnetizable fabric or the prosthesis   722

writing information on the implantable magnetizable fabric, the information comprising second information comprises information corresponding to at least one of the subject or a health care provider   724

FIG. 8

DATA STORAGE ON IMPLANTABLE MAGNETIZABLE FABRIC

RELATED APPLICATION

This application claims priority to Provisional Patent Application No. 62/719,354, filed on Aug. 17, 2018, which is incorporated by reference in its entirety.

BACKGROUND

1. Technical Field

The present disclosure relates to a system, a device, and a method for storing data on implantable magnetizable fabric. In particular, the present disclosure relates to data storage on implantable magnetizable fabric used for an implantable device or a prosthesis.

2. Background Information

An implantable device or a prosthesis, for example but not limited to a graft stent in the field of aortic intervention may be delivered into a patient with vascular diseases including peripheral and cardiovascular diseases, for example, stroke, cerebral hemorrhage, and aneurysms. The graft stent may be placed inside the patient for an extended period of time. One of the existing drawbacks is there may not be effective solutions to record information on the graft stent for easy access.

The present disclosure is directed toward addressing one or more drawbacks, including but not limited to those set forth above.

BRIEF SUMMARY

The present disclosure is directed to A system for storing data on a prosthesis, the system comprising: implantable magnetizable fabric coupled to a graft segment of a prosthesis for being delivered into a body of a subject; information written on the implantable magnetizable fabric; and a magnetic detection device capable of, after the prosthesis is delivered into the body of the subject, detecting the implantable magnetizable fabric and accessing at least a portion of the information.

The present disclosure also describes an apparatus for storing data on a prosthesis. The apparatus includes implantable magnetizable fabric coupled to a graft segment of a prosthesis for being delivered into a body of a subject. The apparatus also includes information written on the implantable magnetizable fabric. After the prosthesis is delivered into the body of the subject, the implantable magnetizable fabric is detectable by a magnetic detection device and at least a portion of the information is accessible by the magnetic detection device.

The present disclosure also describes a method for storing data on a prosthesis. The method includes coupling implantable magnetizable fabric to a graft segment of a prosthesis for being delivered into a body of a subject. The method also includes writing information on the implantable magnetizable fabric. The method further includes after the prosthesis is delivered into the body of the subject, detecting the implantable magnetizable fabric by a magnetic detection device and accessing at least a portion of the information by the magnetic detection device.

BRIEF DESCRIPTION OF THE DRAWINGS

FIG. 8 is a flow diagram of a method for storing data on a prosthesis

DETAILED DESCRIPTION OF THE DRAWINGS

Figure 1:
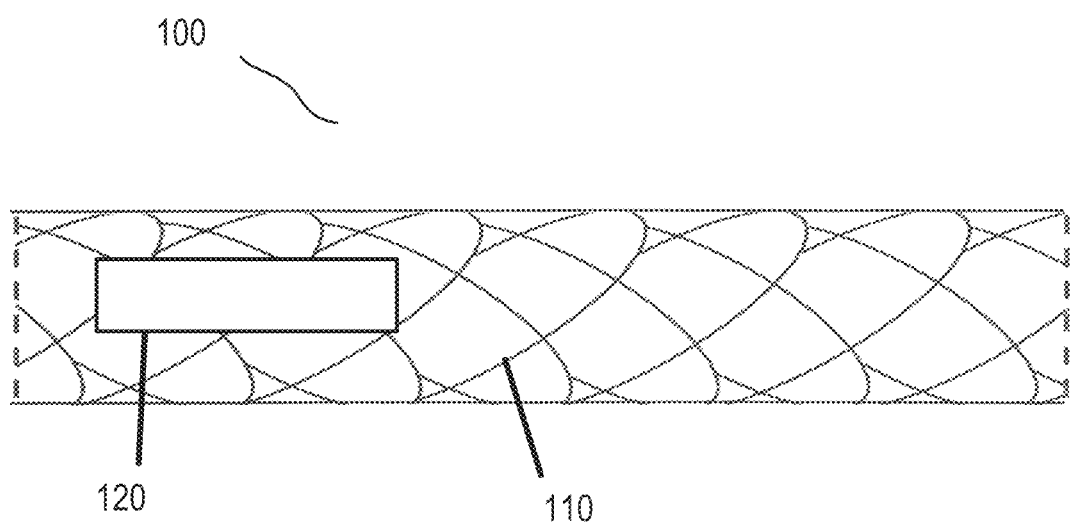
FIG. 1 is a schematic diagram of a prosthesis with a magnetizable fabric on a stent.

The invention will now be described in detail hereinafter with reference to the accompanied drawings, which form a part of the present invention, and which show, by way of illustration, specific examples of embodiments. Please note that the invention may, however, be embodied in a variety of different forms and, therefore, the covered or claimed subject matter is intended to be construed as not being limited to any of the embodiments to be set forth below. Please also note that the invention may be embodied as methods, devices, components, or systems. Accordingly, embodiments of the invention may, for example, take the form of hardware, software, firmware or any combination thereof.

Throughout the specification and claims, terms may have nuanced meanings suggested or implied in context beyond an explicitly stated meaning. Likewise, the phrase "in one embodiment" or "in some embodiments" as used herein does not necessarily refer to the same embodiment and the phrase "in another embodiment" or "in other embodiments" as used herein does not necessarily refer to a different embodiment. It is intended, for example, that claimed subject matter includes combinations of exemplary embodiments in whole or in part.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B or C, is intended to mean A, B, and C, here used in the inclusive sense, as well as A, B or C, here used in the exclusive sense. In addition, the term "one or more" or "at least one" as used herein, depending at least in part upon context, may be used to describe any feature, structure, or characteristic in a singular sense or may be used to describe combinations of features, structures or characteristics in a plural sense. Similarly, terms, such as "a", "an", or "the", again, may be understood to convey a singular usage or to convey a plural usage, depending at least in part upon context. In addition, the term "based on" or "determined by" may be understood as not necessarily intended to convey an exclusive set of factors and may, instead, allow for existence of additional factors not necessarily expressly described, again, depending at least in part on context.

When an implantable device or a prosthesis, for example but not limited to a stent, is delivered to a treatment location in a subject by a health care provider, it may be desirable that the location of the stent can be easily detected and information can be stored on the stent graft so that the information can be retrieved later by the same health care provider or another health care provider. It also may be desirable that new information can be stored on the stent graft later by the same health care provider or another health care provider.

In the description below, a stent is used as an example to illustrate the embodiments. The present disclosure may include any other types of implantable devices or prostheses, and is not limited to the stent.

In this disclosure, a stent cover materials include a magnetizable fabric. This fabric can be magnetized from outside or inside the stent to record information. The information may be written on the magnetizable fabric, and can be accessed from the magnetizable fabric at a later time point. In other embodiment, the information on the magnetizable fabric may be erasable so that new information may be written on the magnetizable fabric. There is no need of continuous electrical power for storing the information on the magnetic fabric.

A portion of the information may be written on the magnetizable fabric by a manufacturer before the stent is shipped from the manufacture or by the health care provider before the stent is delivered into the subject. A portion of the information may be written by the same or a different health care provider after the stent is delivered into the subject.

FIG. 1 shows an embodiment of a piece of magnetizable fabric 120 on an implantable device or a prosthesis 100. In one embodiment, the implantable device or the prosthesis 100 may be a stent. The stent 100 may have a stent frame 110.

The piece of magnetizable fabric 120 may be embedded as a part of the stent cover, may be attached to an outside surface of the stent cover, or may be attached to an inside surface of the stent cover.

The information on the magnetizable fabric may be accessed from either outside the stent or inside the stent tube. The information on the magnetizable fabric may be written, read, erased or rewritten as needed from outside the stent or from inside the stent tube by a device.

Figure 2:
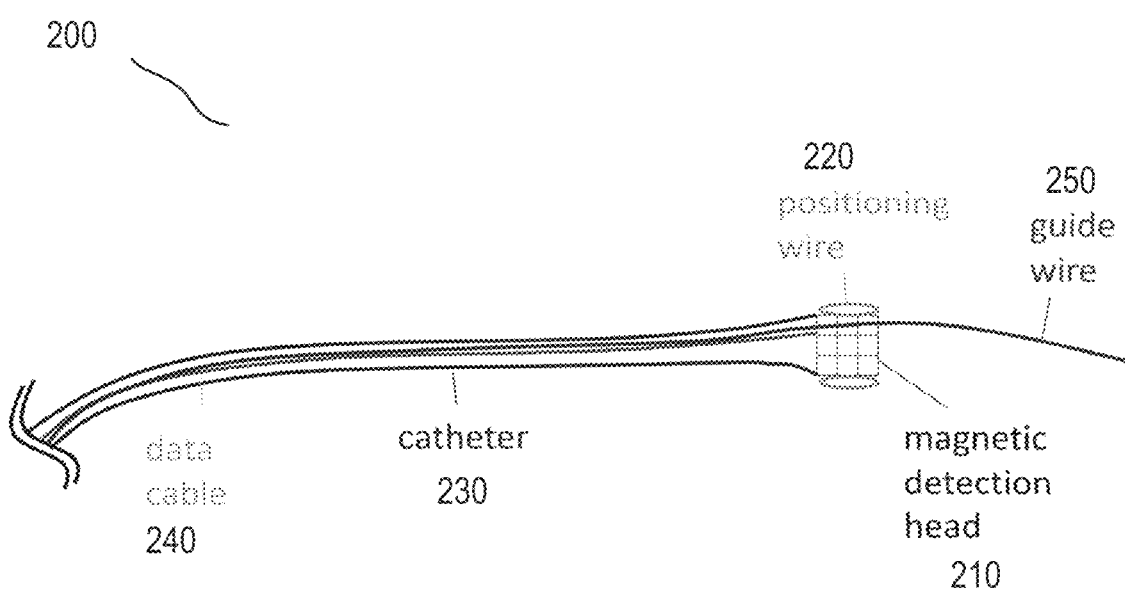
FIG. 2 is a schematic diagram of a device for accessing information on a magnetizable fabric on a prosthesis.

FIG. 2 shows an embodiment of a device 200, which can access information on the magnetizable fabric from inside the stent. The device 200 may include a magnetic head 210, which can read, write, erase or rewrite information on the magnetizable fabric from inside the stent. In one embodiment, the magnetic head 210 may be a magnetic detection head.

The device 200 may also include a catheter 230 and a data cable 240. The data cable 240 transmits data between the magnetic head and a terminal device located outside the body of the patient. The data cable 240 may be disposed inside the catheter 230. A guide wire 250 may extend through a lumen or channel of the catheter 230 and guide the device 200 into the patient.

In another embodiment, the device 200 may include a positioning component 220, for example but not limited to, a positioning wire. When the magnetic head 210 accesses the information on the magnetizable fabric, the positioning component 220 may detect and/or position the magnetic head 210 relative to the magnetizable fabric.

In one embodiment, a position code may be written on the magnetizable fabric. When the position code is detected by the positioning component 220, the device 200 may determine the position of the magnetic head 210 relative to the magnetizable fabric, and then adjust its position. The position code may include coordinate information, for example but not limited to, coordinate parameters of Cartesian coordinate system, or coordinate parameters of cylindrical coordinate system.

In another embodiment, a position of the magnetic head 210 inside the stent may be detected through correlation methods. Similar as optical positioning of a caliper or a Computer Numerical Control (CNC) machine, positional information may be encoded on the magnetized fabric with a magnetic pattern. The positional information may include distance information of the magnetic pattern on the magnatized fabric. A correction method may be used to increase reliability. The correction method may include, but not be limited to, Viterbi algorithm.

The information may include a production of the stent graft, including but not limited to, a name of the manufacturer, a type of the stent, a model of the stent, a serial number of the stent, dimensional parameters of the stent, a manufacture date of the stent, materials of the stent and stent cover. The information may include storage conditions of the stent, including but not limited to, a storage temperature and a storage humidity. The information may also include transportation conditions of the stent, including but not limited to, temperature and humidity during transportation.

The information may also include information related to the subject. The subject may be a patient, and the information related to the subject may include the patient's recent conditions, long-term health conditions, other contemporaneous patient information including the parameters affecting stent customization, or any note related to the subject. In another embodiment, the information related to the subject may include the position of the stent or an orientation of the stent inside the subject. The orientation of the stent may include a right angle, a left angle, a distal angle, or a proximal angle.

The information may also include information of the health care provider. The information of the health care provider may include a name of the health care provider, a name of a physician, a date of stent delivery operation, conditions during stent delivery, procedure steps during stent delivery operation, any note related to the stent or the health care provider.

In one embodiment, a magnetizable fabric may contain magnetic beads. The magnetic beads may be magnetized at various polarization or various degree of magnetic field strength, which may be used to code information. The magnetic beads may be nanobeads with diameters between around 50 nanometer and around 500 nanometer. The magnetic beads may also be microbeads with diameters between around 0.5 micrometer and 500 micrometer. A size of a single magnetic pixel to store a single unit of information may be as small as around 5 micrometer by around 5 micrometer. The magnetic beads may be made from magnetic materials, including but not limited to, $MFe_2O_4$, Co, Fe, FePt, CoPt, CoFe, or $SmCo_5$.

In another embodiment, a magnetizable fabric may be made from magnetic fibers. The magnetic fibers may comprise a yarn sizes between around 10 Denier and around 40 Denier. A size of a single magnetic pixel to store a single unit of information may be as small as around 10 micrometer by around 10 micrometer. The magnetic fibers may be made, including but not limited to, of BK 50/2, VN 140 nyl/35×3, Aracon, Bekintex single-ply, or Ferromagnetic BCP Conductive Sewing Thread.

The present disclosure also describes several methods of producing a magnetizable fabric. In one embodiment, a magnetizable fabric may be produced by firstly magnetizing yarns and then weaving the magnetized yarns into fabric. In another embodiment, a magnetizable fabric may be produced by firstly weaving magnetic yarns and then be magnetized.

Magnetic yarns or magnetic beads may be magnetized with a positive polarity, a negative polarity, or zero polarity (i.e, not magnetized). The magnetic yarns or magnetic beads may be magnetized at different magnetic field strength, i.e., having different degree of magnatization. The magnetic yarns may be magnetized continuously or non-continuously.

In another embodiment, a magnetic printing machine may be used to write information on the magnetizable fabric. The magnetic printing machine may use method of polymagnetization to magnetize magnetic yarns or magnetic beads.

The present disclosure also describes methods of encoding information on the magnetizable fabric. The information could be text information, picture information, or audio/video information. A single unit of information may be encoded on a single magnetic pixel using binary coding or multi-level coding.

Figure 3:
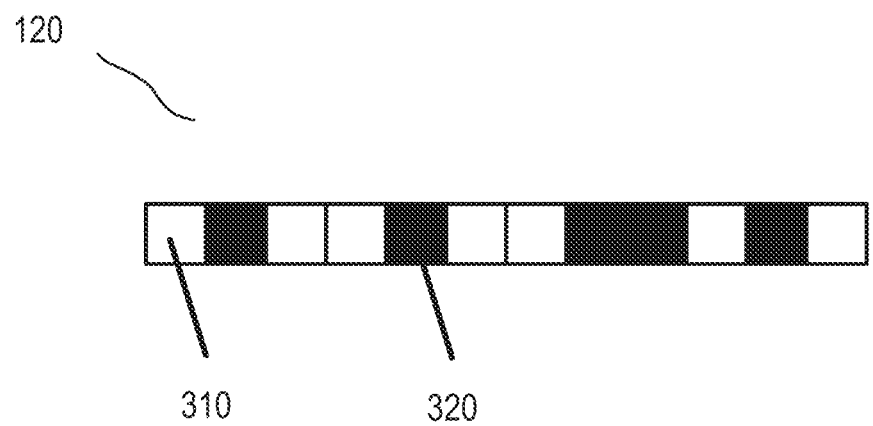
FIG. 3 is a schematic diagram of a binary-level coding on a magnetizable fabric.

In one embodiment, as shown in FIG. 3, a single unit of information may be encoded on a single magnetic pixel using binary coding. For example, a binary code "0" may be represented by a magnetic pixel 310 and a binary code "1" may be represented by a magnetic pixel 320 or vice versa.

In another embodiment, the binary coding may depend on a magnetic polarity. The magnetic pixel 310 may be magnetized with a positive polarity and the magnetic pixel 320 may be magnetized with a negative polarity or vice versa.

In another embodiment, the binary coding may depend on a magnetic field strength. The magnetic 310 may be magnetized with a magnetic field strength below a certain low threshold and the magnetic pixel 320 may be magnetized with a magnetic field strength above a certain high threshold or vice versa.

Figure 4:
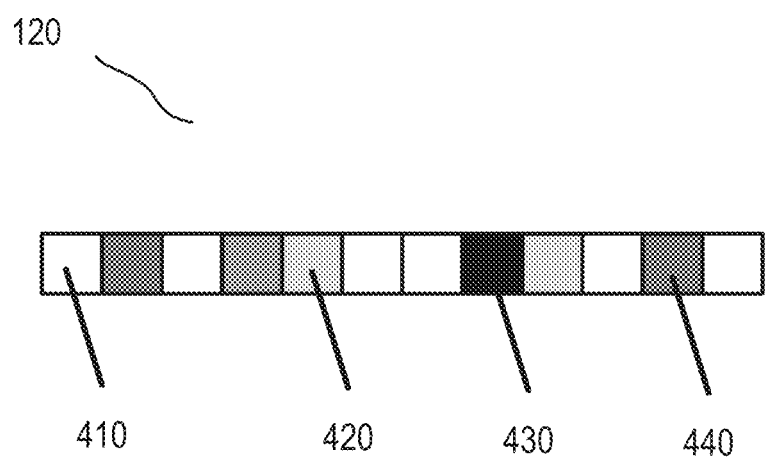
FIG. 4 is a schematic diagram of a multiple-level coding on a magnetizable fabric.

In one embodiment, as shown in FIG. 4, a multiple-level coding based on magnetic field strength may be used to encode information on magnetic pixels. The magnetic field strength of the magnetic pixels may be between a range, which can be divided into more than two segments, for example, 4 segments or 10 segments. Each segment of magnetic field strength may be used to encode a specific information.

For example, the range may be from zero to 60 microTesla, which may be divided into 4 segments. The first segment with magnetic field strength larger than or equal to zero and smaller than 15 microTesla represents code "0", for example as for the magnetic pixel 410. The second segment with magnetic field strength larger than or equal to 15 microTesla and smaller than 30 microTesla represents code "1", for example as for the magnetic pixel 420. The third segment with magnetic field strength larger than or equal to 30 microTesla and smaller than 45 microTesla represents code "2", for example as for the magnetic pixel 440. The fourth segment with magnetic field strength larger than or equal to 45 microTesla and smaller than or equal to 60 microTesla represents code "4", for example as for the magnetic pixel 430.

Figure 5:
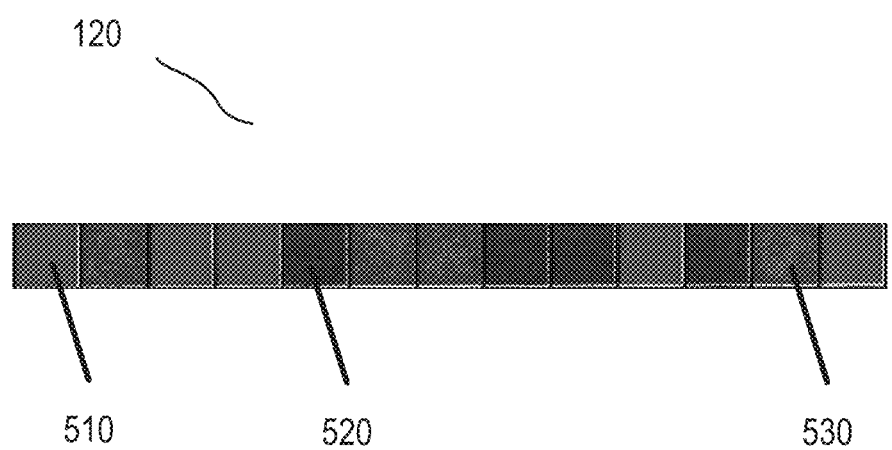
FIG. 5 is a schematic diagram of another multiple-level coding on a magnetizable fabric.

In another embodiment, as shown in FIG. 5, a multiple-level coding based on both magnetic field strength and magnetic polarity may be used to encode information on magnetic pixels. The magnetic field with different polarity may be assigned as positive and negative values corresponding to the magnetic field strength. For example, magnetic fields with positive polarity have positive values and magnetic fields with negative polarity have negative values. The magnetic field strength with polarity of the magnetic pixels may be between a range, which can be divided into more than two segments, for example, 4 segments or 10 segments. Each segment of magnetic field strength may be used to encode a specific information.

For example, the range of the magnetic field strength with polarity may be from −60 to 60 microTesla, which may be divided into 4 segments. The first segment with magnetic field strength larger than or equal to −60 and smaller than −30 microTesla represents code "0", for example as for the magnetic pixel 530. The second segment with magnetic field strength larger than or equal to −30 microTesla and smaller than 0 microTesla represents code "1". The third segment with magnetic field strength larger than or equal to 0 microTesla and smaller than 30 microTesla represents code "2", for example as for the magnetic pixel 520. The fourth segment with magnetic field strength larger than or equal to 30 microTesla and smaller than or equal to 60 microTesla represents code "4", for example as for the magnetic pixel 510.

Figure 6:
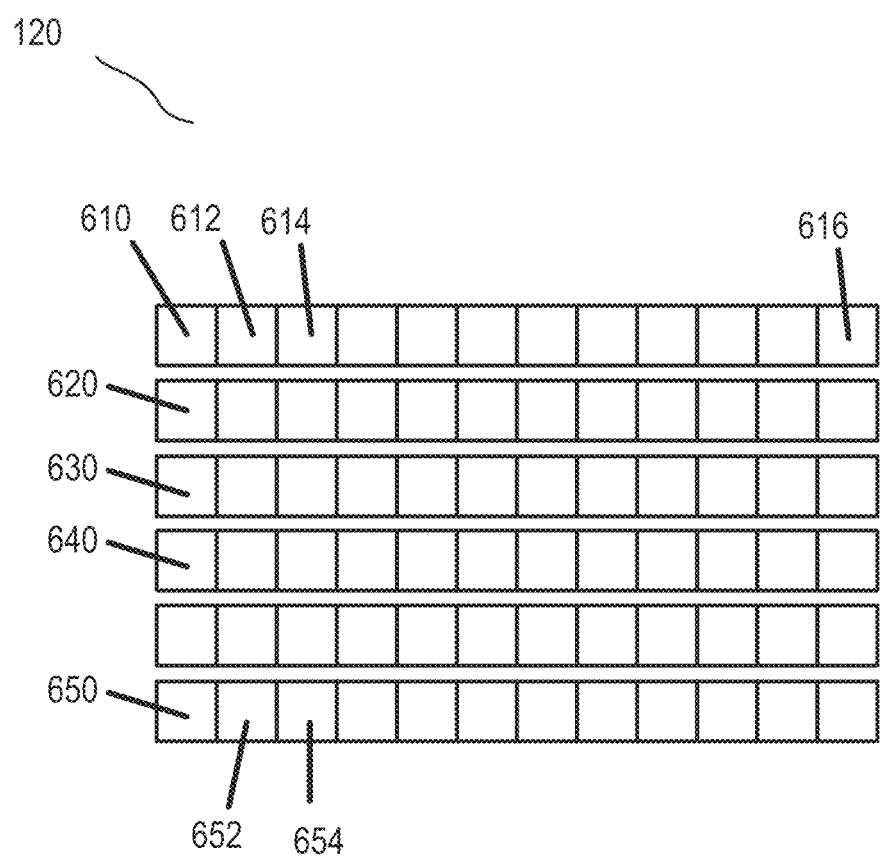
FIG. 6 is a schematic diagram of a coding pattern on a magnetizable fabric.

In one embodiment, as shown in FIG. 6, magnetic pixels on a magnetizable fabric 120 may be arranged as an array. The array may have a first number of rows and a second number of columns. When information is encoded on the magnetic pixels, one method of sequentially encoding the information may be to encode the rows first, and then the columns. For example, the first unit of information is encoded on a magnetic pixel 610, and then second unit of information is encoded on a magnetic pixel 612, followed by a magnetic pixel 614. Following the last magnetic pixel 616 of the first row, the first magnetic pixel 620 of the second row sequentially stores the next unit of the information. Then the second row of magnetic pixels are encoded sequentially as needed.

When information is encoded on the magnetic pixels, another method of sequentially encoding the information may be to encode the columns first, and then the rows. For example, the first unit of information is encoded on a magnetic pixel 610, and then second unit of information is encoded on a magnetic pixel 620, followed by a magnetic pixel 630 and a magnetic pixel 640, respectively. Following the last magnetic pixel 650 of the first column, the first magnetic pixel 612 of the second column sequentially stores the next unit of the information. Then the second column of magnetic pixels are encoded sequentially as needed, until the last magnetic pixel 652 of the second column is encoded.

The present disclosure also describes a method of encoding a two-dimensional image on a magnetizable fabric on an implantable device or a prosthesis, for example but not limited to a stent. The two-dimensional image may include one of a picture, a schematic diagram, a drawing, a chart, a two-dimensional bar code, or a two-dimensional Quick Response (QR) code. The two-dimensional image may be encoded sequentially on magnetic pixels as described above, or may be directly encoded as a two-dimensional image on an array of magnetic pixels.

The present disclosure also describes a method for storing data on a tube of an implantable device or a prosthesis, for example but not limited to a stent graft. The method includes using a system for storing data on the prosthesis. The system may be any of the embodiments as described above.

Figure 7:
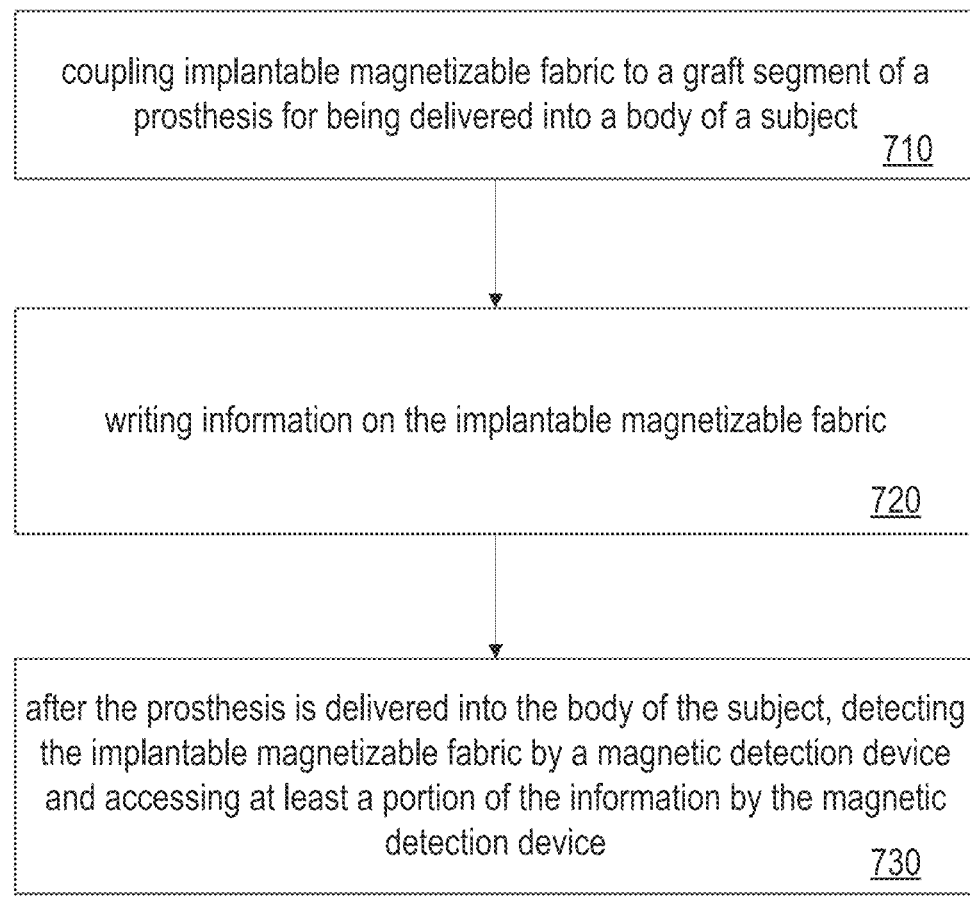
FIG. 7 is a flow diagram of a method for storing data on a prosthesis.

In one embodiment, a method for storing data on a prosthesis is shown in FIG. 7. The method includes step 710: disposing implantable magnetizable fabric on a prosthesis for being delivered into a body of a subject.

The method also includes step 720: writing information on the implantable magnetizable fabric. In one embodiment, the step 720 may include step 722 in FIG. 8: writing information on the implantable magnetizable fabric, the information comprising first information, the first information comprising information corresponding to at least one of the implantable magnetizable fabric or the prosthesis. The step 720 may also include step 724 in FIG. 8: writing information on the implantable magnetizable fabric, the information comprising second information, the second information comprising information corresponding to at least one of the subject or a health care provider.

The method further includes step 730: after the prosthesis is delivered into the body of the subject, detecting the implantable magnetizable fabric by a magnetic detection device and accessing at least a portion of the first information or the second information by the magnetic detection device.

While the particular invention has been described with reference to illustrative embodiments, this description is not meant to be limiting. Various modifications of the illustrative embodiments and additional embodiments of the invention will be apparent to one of ordinary skill in the art from this description. Those skilled in the art will readily recognize that these and various other modifications can be made to the exemplary embodiments, illustrated and described herein, without departing from the spirit and scope of the present invention. It is therefore contemplated that the appended claims will cover any such modifications and alternate embodiments. Certain proportions within the illustrations may be exaggerated, while other proportions may be minimized. Accordingly, the disclosure and the figures are to be regarded as illustrative rather than restrictive.

The invention claimed is:

1. An apparatus for storing data on a prosthesis, the apparatus comprising:
   implantable magnetizable fabric coupled to a graft segment of a prosthesis for being delivered into a body of a subject;
   information written on the implantable magnetizable fabric; and
   wherein:
      after the prosthesis is delivered into the body of the subject, the implantable magnetizable fabric is detectable by a magnetic detection device and at least a portion of the information is accessible by the magnetic detection device;
      the magnetic detection device comprises a data cable, a catheter, and a head;
      the head is configured to access a portion of the information;
      the data cable is disposed inside the catheter; and
      the magnetic detection device is delivered inside the prosthesis to access at least the portion of the information.

2. The apparatus according to claim 1, wherein:
   the information comprises first information and second information;
   the first information comprises information corresponding to at least one of the implantable magnetizable fabric or the prosthesis; and
   the second information comprises information corresponding to at least one of the subject or a health care provider.

3. The apparatus according to claim 1, wherein:
   the information comprises at least one of a text or an image;
   the information is capable of being encoded as one of binary codes or multi-level codes; and
   the implantable magnetizable fabric comprises magnetic beads or magnetic fiber.

4. The apparatus according to claim 1, wherein:
   the prosthesis comprises a stent graft; and
   the graft segment comprises a tube of the stent graft.

5. The apparatus according to claim 1, wherein:
   at least one position code is written on the implantable magnetizable fabric, and the at least one position code is detected by a positioning component of the magnetic detection device to position the magnetic detection device relative to the implantable magnetizable fabric.

6. A system for storing data on a prosthesis, the system comprising:
   implantable magnetizable fabric coupled to a graft segment of a prosthesis for being delivered into a body of a subject;
   information written on the implantable magnetizable fabric; and
   a magnetic detection device capable of, after the prosthesis is delivered into the body of the subject, detecting the implantable magnetizable fabric and accessing at least a portion of the information, wherein:
      the magnetic detection device comprises a data cable, a catheter, and a head;
      the head is configured to access a portion of the information;
      the data cable is disposed inside the catheter; and
      the magnetic detection device is delivered inside the prosthesis to access at least the portion of the information.

7. The system according to claim 6, wherein:
   the information comprises first information and second information;
   the first information comprises information corresponding to at least one of the implantable magnetizable fabric or the prosthesis; and
   the second information comprises information corresponding to at least one of the subject or a health care provider.

8. The system according to claim 6, wherein:
   the information comprises at least one of a text or an image.

9. The system according to claim 6, wherein:
   the information is capable of being encoded as one of binary codes or multi-level codes.

10. The system according to claim 6, wherein:
    the prosthesis comprises a stent graft; and
    the graft segment comprises a tube of the stent graft.

11. The system according to claim 6, wherein:
    at least one position code is written on the implantable magnetizable fabric;
    the magnetic detection device comprises a positioning component to detect the at least one position code to position the magnetic detection device relative to the implantable magnetizable fabric.

12. The system according to claim 6, wherein:
    the implantable magnetizable fabric comprises magnetic beads or magnetic fiber.

* * * * *